United States Patent [19]

Manner et al.

[11] Patent Number: 5,858,285
[45] Date of Patent: Jan. 12, 1999

[54] PROCESS FOR THE PRODUCTION OF AN AQUEOUS SOLUTION OF A TERTIARY AMINE-OXIDE

[75] Inventors: Johann Manner, Weyregg; Heinrich Firgo, Vocklabruck; Bruno Mangeng, Seewalchen; Eduard Mulleder, Linz; Wolfram Kalt, Lenzing, all of Austria

[73] Assignee: Lenzing Aktiengesellschaft, Lenzing, Austria

[21] Appl. No.: 843,395

[22] Filed: Apr. 15, 1997

Related U.S. Application Data

[63] Continuation-in-part of PCT/AT96/00148 and PCT/AT96/00149 both filed Aug. 16, 1996.

[30] Foreign Application Priority Data

Aug. 18, 1995 [AT] Austria ..................................... 1399/95
Aug. 18, 1995 [AT] Austria ..................................... 1400/95

[51] Int. Cl.⁶ .............................. D01F 2/02; D01F 13/02
[52] U.S. Cl. .......................................... 264/37.2; 264/187
[58] Field of Search ................................. 264/37.2, 187, 264/203

[56] References Cited

U.S. PATENT DOCUMENTS 5,628,941 5/1997 Kalt et al. ............................... 264/37.2

OTHER PUBLICATIONS

Stupavska, Act Fac. Rer. Nat. Univ. Comen. Chimia., 1980 pp. 85–101.
Firgo et al., Lenzinger Berichte, vol. 9, Sep. 1994, pp. 80–88.
Abstract of E.P.O. 356,419 (Published Feb. 28, 1990).
Abstract of E.P.O. 553,070 (Published Jul. 28, 1993).
Abstract of WO97/7268 (Published Feb. 27, 1997).

*Primary Examiner*—Leo B. Tentoni
*Attorney, Agent, or Firm*—Baker & Botts LLP

[57] ABSTRACT

The invention is concerned with a process for the production of an aqueous amine-oxide solution used in the amine-oxide process for the production of a mouldable cellulose solution, wherein aqueous, amine-oxide containing solutions produced in said amine-oxide process particularly as precipitation baths are purified and concentrated, characterized in that a microbiocide agent is added to said aqueous, amine-oxide containing solutions before, during or after purification.

12 Claims, No Drawings

PROCESS FOR THE PRODUCTION OF AN AQUEOUS SOLUTION OF A TERTIARY AMINE-OXIDE

CROSS-REFERENCE TO RELATED APPLICATIONS

This application is a continuation-in-part of PCT/AT96/00148 and PCT/AT96/00149, both filed Aug. 16, 1996, now abandoned, both of which are incorporated by reference herein.

INTRODUCTION

The present invention is concerned with a process for the production of an aqueous amine-oxide solution used in the amine-oxide process for the production of a mouldable cellulose solution, wherein aqueous, amine-oxide containing solutions produced in the amine-oxide process particularly as precipitation baths are purified and concentrated.

BACKGROUND OF THE INVENTION

For some decades there has been searched for processes for the production of cellulose moulded bodies able to substitute the viscose process, today widely employed. As an alternative which is interesting for its reduced environmental impact among other reasons, it has been found to dissolve cellulose without derivatisation in an organic solvent and extrude from this solution moulded bodies, e.g. fibres, films and other moulded bodies. Fibres thus extruded have received by BISFA (The International Bureau for the Standardization of man made fibers) the generic name Lyocell. By an organic solvent, BISFA understands a mixture of an organic chemical and water.

It has turned out that as an organic solvent, a mixture of a tertiary amine-oxide and water is particularly appropriate for the production of cellulose moulded bodies. As the amine-oxide, primarily N-methylmorpholine-N-oxide (NMMO) is used. Other amine-oxides are described e.g. in EP-A-0 553 070. A process for the production of mouldable cellulose solutions is known e.g. from EP-A-0 356 419. For the purposes of the present specification and the present claims, the production of cellulose moulded bodies using tertiary amine-oxides generally is referred to as amine-oxide process.

In EP-A-0 356 419, an amine-oxide process for the production of spinnable cellulose solutions is described, wherein as a starting material among others a suspension of cellulose in liquid, aqueous N-methylmorpholine-N-oxide (NMMO) is used. This process consists in transforming the suspension in a thin-film treatment apparatus in one single step and continuously into a mouldable solution. Finally, the mouldable solution is spun into filaments by a forming tool such as a spinneret and the filaments are passed through a precipitation bath.

In the precipitation bath the cellulose is precipitated. The tertiary amine-oxide is accumulated in the precipitation bath. The precipitation bath may contain up to 30% by weight of amine-oxide. For the economy of the amine-oxide process it is of vital importance to recover the amine-oxide as completely as possible and reuse it for the production of a mouldable cellulose solution. Thus it is necessary to recover NMMO from the precipitation bath.

In addition to the amine-oxide however, degradation products of the amine-oxide are also accumulated in the precipitation bath. These degradation products may be intensively coloured, thus deteriorating the quality of the cellulose moulded bodies produced. On the other hand, other substances may represent an additional safety risk, since under certain conditions the amine-oxide tends to show highly exothermic decomposition reactions and these decomposition reactions may be induced or accelerated by certain substances. These substances have to be removed from the precipitation bath which is to be regenerated before the NMMO is concentrated and separated in accordance with purification process described in WO 97/07268.

In addition to these substances, in the amine-oxide process also substances in a colloidal state may occur. Moreover, coatings may form at the walls of pipes and the like which may impair the flow and may even lead to an obstruction of the pipe.

After removing these unwanted substances, water is withdrawn from the purified precipitation bath which optionally is combined with other process liquids of the amine-oxide process such as vapour condensates formed during the production of the cellulose solution. This may be carried out for instance by means of evaporation. In the residue of this evaporation, highly concentrated aqueous amine-oxide is produced which is recycled again into the amine-oxide process.

BRIEF SUMMARY OF THE INVENTION

In the state of the art, no step is known whereby the above formation of coatings at walls of pipes can be effectively prevented. It is the object of the present invention to carry out the amine-oxide process such that the formation of these coatings is prevented.

The process according to the invention for the production of an aqueous amine-oxide solution used in the amine-oxide process for the production of a mouldable cellulose solution, wherein aqueous, amine-oxide containing solutions produced in the amine-oxide process particularly as precipitation baths are purified and concentrated, is characterized in that a microbiocide agent is added to the aqueous, amine-oxide containing solutions before, during or after purification.

DETAILED DESCRIPTION OF THE INVENTION

The invention is based on the finding that the formation of coatings is caused by microorganisms and consists substantially of biological substances. As microorganisms, particularly bacteria, yeasts, fungi and algae have been found. This is surprising since for some decades it was considered that tertiary amine-oxides generally have a microbicide effect (Stupavska, S., Acta Fac. Rer. Nat. Univ. Comen, 1980, pages 85 ff) and that they are not biodegradable. Only recently it has been found out that NMMO can be degraded in a biological sewage plant (H. Firgo, M. Eibl, W. Kalt, G. Meister: Kritische Fragen zur Zukunft der NMMO-Technologie, Lenzinger Berichte 9/94, pages 81 ff). Therefore it is all the more surprising for those skilled in the art that microorganisms are capable of surviving in a variety of NMMO solutions of the amine-oxide process wherein NMMO is present in a much higher concentration than in a sewage plant, may even propagate and thus cause the formation of coatings.

When a microbiocide agent acting on these microorganisms is added to the amine-oxide process, the formation of the unwanted biological substances and thus the formation of wall coatings may be effectively prevented.

As microbiocide agents, preferably fungicides, algicides and bactericides are used.

As microbiocide agents, the following agents have shown particularly good results: agents of the aliphatic aldehyde group, aromatic aldehydes, thiadiazin derivatives, tetramethylolacetylen urea, hydroxy ethylphenyl ethers, organobromine compounds, polyhexamethylene-biguanide-hydrochloride, sodium azide, hydrogen peroxide and peracetic acid, ortho-phthalaldehyde or glutaraldehyde being particularly preferred.

It is evident to those skilled in the art that the type and concentration of the microbiocide agents will vary for each individual case. The effective dosage for each individual case however may be easily determined by testing. It has been shown that the effective amount generally lies in the range of from 10 to 500 ppm.

The invention is further concerned with a process for the production of cellulose moulded bodies according to the amine-oxide process, wherein a cellulose suspension and finally a mouldable solution are produced from an aqueous solution of an amine-oxide and shredded cellulose, which solution is moulded and passed into a precipitation bath, a spent precipitation bath and cellulose moulded bodies being produced, said spent precipitation bath being purified and repassed to an aqueous solution of the amine-oxide which is repassed to the amine-oxide process, characterized in that the process is carried out at least partially in the presence of a microbiocide agent.

By means of the following Examples, the invention will be described in more detail.

EXAMPLE 1 (CONTROL)

A spent precipitation bath of the NMMO process containing 20% by weight of NMMO was lightly shaken for 24 hours at 25° C. Afterwards, the germination index/ml was determined by means of the test described below.

Determination of the germination index/ml

To determine the germination index/ml, 1 ml of each of the solutions was pipetted into a sterile Petri dish and carefully mixed with agar medium. Afterwards the samples were incubated for 3 days at 37° C. After incubation, the entire surface of the Petri dish was counted for germs with the naked eye, and the number obtained was based on 1 ml of sample.

Dishes exhibiting 20 to 300 germs may be evaluated. When more germs were present, the determination was repeated in an appropriate dilution.

A germination index/ml of 2,200,000 was determined.

To determine the effect of microbiocide agents, Example 1 was repeated with the substances indicated in the Table using the indicated concentrations. The germination indices obtained in each case are also shown in the Table.

TABLE

| Example | Substance | Concentration (ppm) | Germination index/ml |
|---|---|---|---|
| 1 | — | — | 2,200,000 |
| 2 | A | 00 | 0 |
| 3 | A | 100 | 0 |
| 4 | A | 20 | 3 |
| 5 | B | 1,000 | 0 |
| 6 | B | 100 | 3 |
| 7 | B | 20 | 164 |
| 8 | C | 1,000 | 0 |
| 9 | C | 100 | 160,000 |
| 10 | C | 20 | 790,000 |
| 11 | D | 1,000 | 1,800 |

TABLE-continued

| Example | Substance | Concentration (ppm) | Germination index/ml |
|---|---|---|---|
| 12 | D | 100 | 460,000 |
| 13 | D | 20 | 1,330,000 |
| 14 | E | 1,000 | 8,200 |
| 15 | F | 1,000 | 87 |

A = ortho-phthalaldehyde;
B = glutaraldehyde;
C = 3,5-dimethylperhydro-1,3,5-thiadiazine-2-thion;
D = tetramethylolacetylendiurea
F = 2,2-dibromo-3-nitrilo-propionamide.

Similarly good results could be obtained with polyhexamethylenbiguanid-hydrochloride and sodium azide.

We claim:

1. A process for the production of an aqueous amine-oxide solution used in the amine-oxide process for the production of a mouldable cellulose solution, comprising the steps of:
   providing a precipitation bath including an aqueous amine-oxide solution;
   purifying and concentrating the aqueous, amine-oxide containing solution produced in said amine-oxide process and adding a microbiocide agent to the aqueous, amine-oxide containing solution before purification.

2. A process according to claim 1, wherein the microbiocide agent is selected from the group consisting of fungicides, algicides and bactericides.

3. A process according to claim 2, wherein the microbiocide agent is selected from the group consisting of aliphatic aldehydes, aromatic aldehydes, thiadiazin derivatives, tetramethylolacetylen urea, hydroxy ethylphenyl ethers, organobromine compounds, polyhexamethylene-biguanide-hydrochloride, sodium azide, hydrogen peroxide and peracetic acid.

4. A process according to claim 3, wherein the microbiocide agent comprises ortho-phthalaldehyde or glutaraldehyde.

5. A process for the production of cellulose moulded bodies according to the amine-oxide process, comprising the steps of:
   producing a cellulose suspension from an aqueous solution of an amine-oxide end shredded cellulose;
   forming a mouldable solution from said suspension;
   conveying said mouldable solution to a precipitation bath thereby forming cellulose moulded bodies and producing a spent precipitation bath;
   purifying said spent precipitation bath to regenerate an aqueous solution of said amine-oxide; and
   recycling said aqueous solution in said amine-oxide process; wherein at least one of said steps is carried out in the presence of a microbiocide agent.

6. A process according to claim 1, wherein the amine-oxide comprises N-methylmopholine-N-oxide.

7. A process for the production of an aqueous amine-oxide solution used in the amine-oxide process for the production of a mouldable cellulose solution comprising the steps of:
   providing a precipitation bath including an aqueous amine-oxide solution;
   purifying and concentrating the aqueous amine-oxide containing solution; and,
   adding a microbiocide agent to the aqueous amine-oxide containing solution during purification.

8. A process for the production of an aqueous amine-oxide solution used in the amine-oxide process for the production of a mouldable cellulose solution comprising the steps of:

providing a precipitation bath including an aqueous amine-oxide solution;

purifying and concentrating the aqueous amine-oxide containing solution; and adding a microbiocide agent to the aqueous amine-oxide containing solution after purification.

9. A process according to claim 7 or claim 8, wherein the microbiocide agent is selected from the group consisting of fungicides, algicides and bactericides.

10. A process according to claim 9, wherein the microbiocide agent is selected from the group consisting of aliphatic aldehydes, aromatic aldehydes, thiadiazin, derivatives, tetramethylolacetylen urea, hydroxy ethylphenyl ethers, organobromine compounds, polyhexamethyline-biguanidine-hydrochloride, sodium azide, hydrogen peroxide and peracetic acid.

11. A process according to claim 10, wherein the microbicide agents comprise ortho-phthaladehyde or glutaraldehyde.

12. A process according to claim 7 or claim 8, wherein the amine-oxide comprises N-methylmorpholine-N-oxide.

\* \* \* \* \*

UNITED STATES PATENT AND TRADEMARK OFFICE
CERTIFICATE OF CORRECTION

PATENT NO. : 5,858,285

DATED : January 12, 1999

INVENTOR(S) : Manner et al.

It is certified that error appears in the above-identified patent and that said Letters Patent is hereby corrected as shown below:

ON THE COVER:

[56] References Cited, OTHER PUBLICATIONS:
Under Stupavska, "Act" should read -- Acta --

IN THE CLAIMS

Col. 4, line 43: "end" should read -- and --

Col. 4, line 54: "N-methylmopholine-N-oxide" should read -- N-methylmorpholine-N-oxide --

Col. 5, line 12: "thiadiazin, derivatives," should read -- thiadiazin derivatives, --

Col. 6, line 6: "bicide" should read -- biocide --

UNITED STATES PATENT AND TRADEMARK OFFICE
CERTIFICATE OF CORRECTION

PATENT NO. : 5,858,285
DATED : January 12, 1999
INVENTOR(S) : Manner et al.

It is certified that error appears in the above-identified patent and that said Letters Patent is hereby corrected as shown below:

Col. 2, line 48: "microbicide" should read
-- microbiocide --

Col. 4, line 15: "polyhexamethylenbiguanid-hydrochloride"
should read -- polyhexamethylene-biguanide-hydrochloride --

Signed and Sealed this

Nineteenth Day of September, 2000

Attest:

Q. TODD DICKINSON

*Attesting Officer*   *Director of Patents and Trademarks*